(12) United States Patent
Su et al.

(10) Patent No.: US 8,470,579 B2
(45) Date of Patent: Jun. 25, 2013

(54) STRAINS OF LACTIC ACID BACTERIA FOR PREVENTING NECROTIZING ENTEROCOLITIS

(75) Inventors: Wei-Chih Su, Tainan (TW);
Kuang-Chih Lee, Tainan (TW);
Hsiang-Ling Chen, Tainan (TW);
Hsiao-Li Wu, Tainan (TW)

(73) Assignee: PROMD Biotech. Co., Ltd., Tainan (TW)

( * ) Notice: Subject to any disclaimer, the term of this patent is extended or adjusted under 35 U.S.C. 154(b) by 0 days.

(21) Appl. No.: 13/470,637

(22) Filed: May 14, 2012

(65) Prior Publication Data
US 2012/0294833 A1 Nov. 22, 2012

(30) Foreign Application Priority Data
May 16, 2011 (TW) .............................. 100117110 A (51) Int. Cl.
*C12N 1/20* (2006.01)
*A01N 63/00* (2006.01)

(52) U.S. Cl.
USPC .................. 435/252.1; 435/252.9; 435/252.4; 424/93.4; 424/93.45

(58) Field of Classification Search
None
See application file for complete search history.

*Primary Examiner* — Jennifer McDonald
*Assistant Examiner* — Qing Xu
(74) *Attorney, Agent, or Firm* — Rosenberg, Klein & Lee (57) ABSTRACT

The present invention relates to novel strains of lactic acid bacteria, *Lactobacillus plantarum* subsp. *plantarum* PM-A0087 deposited as NRRL accession number B-50523, *Bifidobacterium longum* PM-A0101 deposited as NRRL accession number B-50525, and *Bifidobacterium bifidum* PM-A0218 deposited as NRRL accession number B-50524.

10 Claims, 5 Drawing Sheets
(5 of 5 Drawing Sheet(s) Filed in Color)

STRAINS OF LACTIC ACID BACTERIA FOR PREVENTING NECROTIZING ENTEROCOLITIS

FIELD OF THE INVENTION

The present invention relates to novel strains of lactic acid bacteria that are effective in preventing necrotizing enterocolitis.

BACKGROUND OF THE INVENTION

Necrotizing enterocolitis (NEC), occurring most often in preterm infants, is a common gastrointestinal disorder with high mortality rate. About 12% of babies weighing less than 3 lbs.-5 oz. (1,500 grams) experience NEC. The symptoms of NEC include poor tolerance to feedings, weight loss, abdominal distention, bloody stools, peritonitis, sepsis, and shock, and severe cases of NEC cause death. Risk factors including prematurity (Wilson R et al., *Am J Dis Child* 136: 814-816, 1982), hypoxia (Kliegman R M, *J Pediatr* 117: S2-S5, 1990), intestinal ischemia (Abanese C T et al., *Semin Pediatr Surg* 4: 200-206, 1995), bacterial infection (Scheifele D W, *J Pediatr* 117: S44 S46, 1990), and formula feeding (Go L L et al., *J Pediatr Surg* 29: 1059-1063, 1994) have been implicated in the pathogenesis of NEC. However, it is not clear exactly what causes NEC.

Treatments for NEC include stopping feedings, supportive therapies, antibiotics for infection, surgery, and etc. However, the risks of surgery for preterm newborns are high and treatment with antibiotics although inhibits the growth of pathogenic bacteria in the gut, but on the other hand hurts other beneficial bacteria, destroying the equilibrium between bacterial species. Therefore, a safe and effective pharmaceutical or dietary composition for prevention or treatment of necrotizing enterocolitis is desired.

BRIEF SUMMARY OF THE INVENTION

The present invention relates to novel strains of lactic acid bacteria, *Lactobacillus plantarum* subsp. *plantarum* PM-A0087 deposited as NRRL accession number B-50523, *Bifidobacterium longum* PM-A0101 deposited as NRRL accession number B-50525, and *Bifidobacterium bifidum* PM-A0218 deposited as NRRL accession number B-50524.

In one aspect, the present invention provides biologically pure culture of a strain of lactic acid bacteria selected from the group consisting of *Lactobacillus plantarum* subsp. *plantarum* PM-A0087 deposited as NRRL accession number B-50523, *Bifidobacterium longum* PM-A0101 deposited as NRRL accession number B-50525, and *Bifidobacterium bifidum* PM-A0218 deposited as NRRL accession number B-50524.

In another aspect, the present invention is based on the unexpected finding that either or combination of the strains of lactic acid bacteria according to the invention, including *Lactobacillus plantarum* subsp. *plantarum* PM-A0087, *Bifidobacterium longum* FM-A0101, and *Bifidobacterium bifidum* PM-A0218, is beneficial for maintaining the intestinal health of preterm infants via oral administration, and effective in prevention of the occurrence of necrotizing enterocolitis (NEC).

Accordingly, the present invention provides a composition for preventing necrotizing enterocolitis (NEC), comprising a biologically pure culture of *Lactobacillus plantarum* subsp. *plantarum* PM-A0087, *Bifidobacterium longum* PM-A0101, *Bifidobacterium bifidum* PM-A0218, or a combination thereof, in an amount effective in preventing NEC. In one example of the present invention, the composition is a pharmaceutical composition or a dietary composition.

In one embodiment of the invention, the composition comprises a biologically pure culture of *Lactobacillus plantarum* subsp. *plantarum* PM-A0087, a biologically pure culture of *Bifidobacterium longum* PM-A0101, and a biologically pure culture of *Bifidobacterium bifidum* PM A0218, wherein the bacterial numbers of these strains are in a ratio of 1:1:1.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

For the purpose of illustrating the invention, there are shown in the drawings embodiments which are presently preferred. It should be understood, however, that the invention is not limited to the preferred embodiments shown.

In the drawings:

FIG. 4A, degree 0, no necrosis; FIG. 4B, degree 1, mild with epithelial sloughing; FIG. 4C, degree 2, moderate with mid-villous necrosis; and FIG. 4D, degree 3, severe with total villous necrosis.

DETAILED DESCRIPTION OF THE INVENTION

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

In one aspect, the present invention provides a biological pure culture of one strain of lactic acid bacteria selected from the group consisting of *Lactobacillus plantarum* subsp. *plantarum* PM-A0087 (the "PM-A0087 strain"), *Bifidobacterium longum* PM-A0101 (the "PM-A0101 strain"), and *Bifidobacterium bifidum* PM-A0218 (the "PM-A0218 strain").

The three lactic bacteria strains, including the PM-A0087 strain, the PM-A0101 strain and the PM-A0218 strain, were deposited under the Budapest Treaty on Jul. 15, 2011 with an International Depositary Authority, the Agricultural Research Culture Collection (NRRL) at 1815 N. University Street, Peoria, Ill., 61601, U.S.A., and have been assigned NRRL accession numbers B-50523, B-50525, and B-50524, respectively.

According to the present invention, it was unexpectedly found that the PM-A0087 strain, the PM-A0101 strain and the PM-A0218 strain are effective in preventing necrotizing enterocolitis (NEC).

Another aspect of the present invention thus provides a composition for preventing necrotizing enterocolitis (NEC), comprising a biologically pure culture of *Lactobacillus plantarum* subsp. *plantarum* PM-A0087. *Bifidobacterium longum* PM-A0101, *Bifidobacterium bifidum* PM-A0218, or a combination thereof, in an amount effective in preventing NEC.

The term "necrotizing enterocolitis (NEC)" as used herein refers to a disorder with acute partial or chronic intestinal ulcer that causes intestinal tissue necrosis, occurring most often in preterm infants.

According to the present invention, the *Lactobacillus plantarum* subsp. *plantarum* PM-A0087 was isolated by screening from a fermentation plant, e.g., a pickled vegetable, or kimchi. The microbiological characteristics of the PM-A0087 strain are shown below:
 (1) Morphological Characteristics:
  (a) Shape and size cell: The bacteria has a rod-like shape with round edge when culturing at 37° C. overnight in MRS broth observed by microscope.
  (b) Motility: non-motile
  (c) Sporulation: non-spore forming
  (d) Gram-strain: positive
  (e) Aerobicity: facultative
 (2) Cultural Characteristics:
  (a) Medium: lactobacillus MRS broth (see Example 1 below), final pH 6.5±0.2
  (b) Cultural condition: 37° C. anaerobic culture
 (3) Physiological Characteristics:
  (a) Catalase: negative
  (b) Oxidase: negative The *Lactobacillus plantarum* subsp. *plantarum* PM-A0087 was deposited under the Budapest Treaty on Jul. 15, 2011 with the Agricultural Research Culture Collection (NRRL) and has been assigned NRRL accession number B-50523.

According to the present invention, the *Bifidobacterium longum* strain *Bifidobacterium longum* PM-A0101 was isolated by screening from newborn infant feces. The microbiological characteristics of the PM-A0101 strain are shown below:
 (1) Morphological Characteristics:
  (a) Shape and size of cell: The bacteria are rod-shaped or Y-shaped when culturing at 37° C. overnight in MRS broth observed by microscope.
  (b) Motility: non-motile
  (c) Sporulation: non-spore forming
  (d) Gram-strain: positive
  (e) Aerobicity: anaerobic
 (2) Cultural Characteristics:
  (a) Medium: *lactobacillus* MRS broth (see Example 1 below), final pH 6.5±0.2
  (b) Cultural condition: 37° C., anaerobic culture
 (3) Physiological Characteristics:
  (a) Catalase: negative
  (b) Oxidase: negative The *Bifidobacterium longum* PM-A0101 was deposited under the Budapest Treaty on Jul. 15, 2011 with the Agricultural Research Culture Collection (NRRL) and has been assigned NRRL accession number B-50525.

According to the present invention, the *Bifidobacterium bifidum* strain *Bifidobacterium bifidum* PM-A0218 was isolated by screening from newborn infant feces. The microbiological characteristics of the PM-A0218 strain are shown below:
 (1) Morphological Characteristics:
  (a) Shape and size of cell: The bacteria are rod-shaped or Y-shaped when culturing at 37° C. overnight in MRS broth observed by microscope.
  (b) Motility: non-motile
  (c) Sporulation: non-spore forming
  (d) Gram-strain: positive
  (e) Aerobicity: anaerobic
 (2) Cultural Characteristics:
  (a) Medium: lactobacillus MRS broth (see Example 1 below), final pH 6.5±0.2
  (b) Cultural condition: 37° C., anaerobic culture
 (3) Physiological Characteristics:
  (a) Catalase: negative
  (b) Oxidase: negative The *Bifidobacterium bifidum* PM-A0218 was deposited under the Budapest Treaty on Jul. 15, 2011 with the Agricultural Research Culture Collection (NRRL) and has been assigned NRRL accession number B-50524.

The present invention provides a composition for preventing NEC. The composition of the present invention may comprise a biologically pure culture of the PM-A0087 strain, a biologically pure culture of the PM-A0101 strain and a biologically pure culture of the PM-A0218 strain, wherein the bacterial numbers or colony-forming units (CFUs) of these strains are in an appropriate ratio providing a good efficacy in preventing NEC. In one example of the invention, the bacterial numbers of these three strains are preferably in a ratio of 1:1:1, or the composition contains $0.1\text{-}10 \times 10^9$ CFU/ml of each strain.

In one preferred embodiment of the present invention, the composition comprises a biologically pure culture of the PM-A0087 strain, a biologically pure culture of the PM-A0101 strain and a biologically pure culture of the PM-A0218 strain, wherein the bacterial numbers of these strains are in a ratio of 1:1:1, or the composition contains about $1 \times 10^9$ CFU/ml of each strain.

In another embodiment, the composition according to the present invention comprises a biologically pure culture of the PM-A0087 strain, a biologically pure culture of the PM-A0101 strain and a biologically pure culture of the PM-A0218 strain, in a ratio of 1:1:1, wherein each strain is of about $1.5 \times 10^9$ CFU/ml bacteria.

According to one embodiment of the present invention, the composition may be administered orally and formulated as any appropriate forms. The composition can be manufactured as food, a drink or a medicament. In addition, a variety of additives can be included. Examples of additives include but are not limited to colorings (e.g., beta-carotene, anatto, tumeric, paprika and FD & C dyes); flavors, aromas, sweeteners; emulsifiers and/or thickening agents; preservatives, vitamins and antioxidants (e.g., vitamins A, C, D, E, B-1, B-5, B-6, zinc, selenium, calcium, alpha-tocopherol, glutathione, butylated hydroxytoluene (BHT), butylated hydroxyanisole (BHA), and cysteine).

In one embodiment of the present invention, the composition is a pharmaceutical composition comprising a biologically pure culture of the PM-A0087 strain, a biologically pure culture of the PM-A0101 strain, a biologically pure culture of the PM-A0218 strain, or a combination thereof, and a pharmaceutically acceptable carrier. The term "pharmaceutically acceptable carrier" as used herein includes, but is not limited to: saline, buffered saline, dextrose, water, glycerol, ethanol or combination thereof.

In another embodiment of the invention, the composition is a dietary composition comprising a biologically pure culture of the PM-A0087 strain, a biologically pure culture of the PM-A0101 strain, a biologically pure culture of the PM-A0218 strain, or a combination thereof. The dietary composition may be in the form of milk, fermented dairy product, drink, sports drink, a nutritional additive, health food, candy, or jelly.

The present invention is further illustrated by the following examples, which are provided for the purpose of demonstration rather than limitation.

Example 1

Screening and Isolation of *Lactobacillus plantarum* subsp. *plantarum* PM-A0087, *Bifidobacterium longum* PM-A0101, and *Bifidobacterium bifidum* PM-A0218

*Lactobacillus plantarum* subsp. *plantarum* PM-A0087
Kimchi sample was added to the following medium:
(1) MRS− anaerobic: to isolate anaerobic or facultative *Lactobacillus*.
(2) MRS− aerobic: to isolate aerobic *Enterococus*.
(3) MRS+ Cysteine-anaerobic: to isolate anaerobic or facultative *Bifidobacterium*.
(4) LBS− anaerobic: to isolate anaerobic or facultative *Lactobacillus*.
(5) LBS+ acetic acid-anaerobic: to isolate anaerobic or facultative *Lactobacillus*.
(6) TS− aerobic: to isolate aerobic *bacillus*.
(7) LB− aerobic: to isolate *E. coli*.
(8) BCP− anaerobic: to isolate blue colony non-lactic acid bacteria.
(9) BCP− aerobic: to isolate yellow colony lactic acid bacteria.

The isolation was carried out by performing a four quadrant streak plate method.

The MRS medium contains (final pH 6.5±0.2):
10.0 g of proteose peptone,
10.0 g of beef extract,
5.0 g of yeast extract,
20.0 of glucose,
1.0 g of sorbitan monooleate (Tween 80),
2.0 g of ammonium citrate,
5.0 g of sodium acetate,
0.1 g of magnesium sulfate,
0.05 g of manganese (II) sulfate,
2.0 g of dipotassium hydrogen phosphate,
15 g of agar, and
1000 mL of distilled/de-ionized water.

Figure 1:
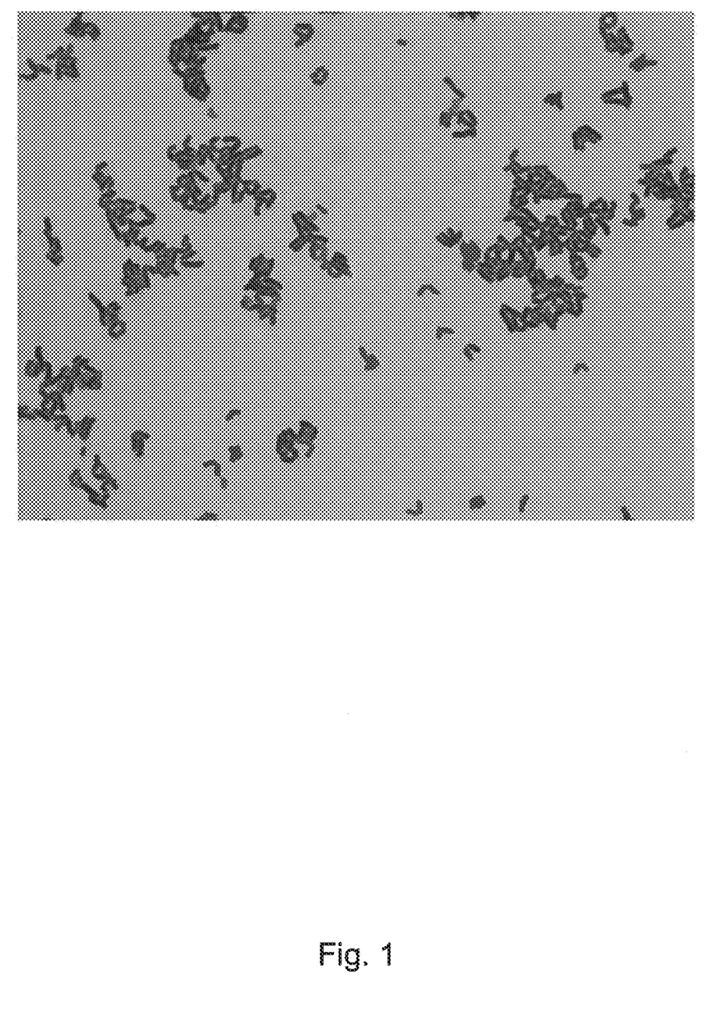
FIG. 1 is a picture of isolated *Lactobacillus plantarum* subs. *plantarum* PM-A0087 under microscope.

A picture of the isolated bacteria under microscope is shown in FIG. 1. The cells of the isolated strain are rod-shaped Gram-positive bacteria. This strain was identified as *Lactobacillus plantarum* subsp. *plantarum* and designated as PM-A0087, which was deposited with the Agricultural Research Culture Collection (NRRL) and have been assigned NRRL accession number B-50523.

*Bifidobacterium longum* PM-A0101
The sample of newborn infant feces was used and followed the same isolation procedure as described above.

Figure 2:
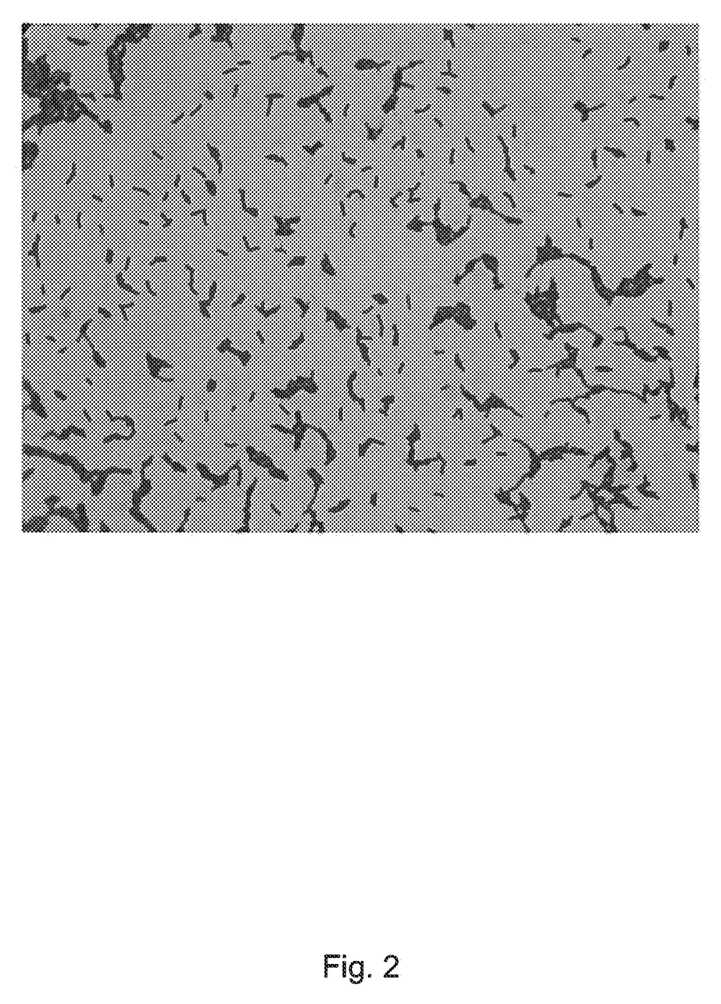
FIG. 2 is a picture of isolated *Bifidobacterium longum* PM-A0101 under microscope.

A picture of the isolated bacteria under microscope is shown in FIG. 2. The cells of the isolated strain are rod-shaped or Y-shaped Gram-positive bacteria. This strain was identified as *Bifidobacterium longum* and designated as PM-A0101, which was deposited with the Agricultural Research Culture Collection (NRRL) and have been assigned NRRL accession number NRRLB-50525.

*Bifidobacterium bifidum* PM-A0218
The sample of newborn infant feces was used and the strain was isolated following the procedures as described above.

Figure 3:
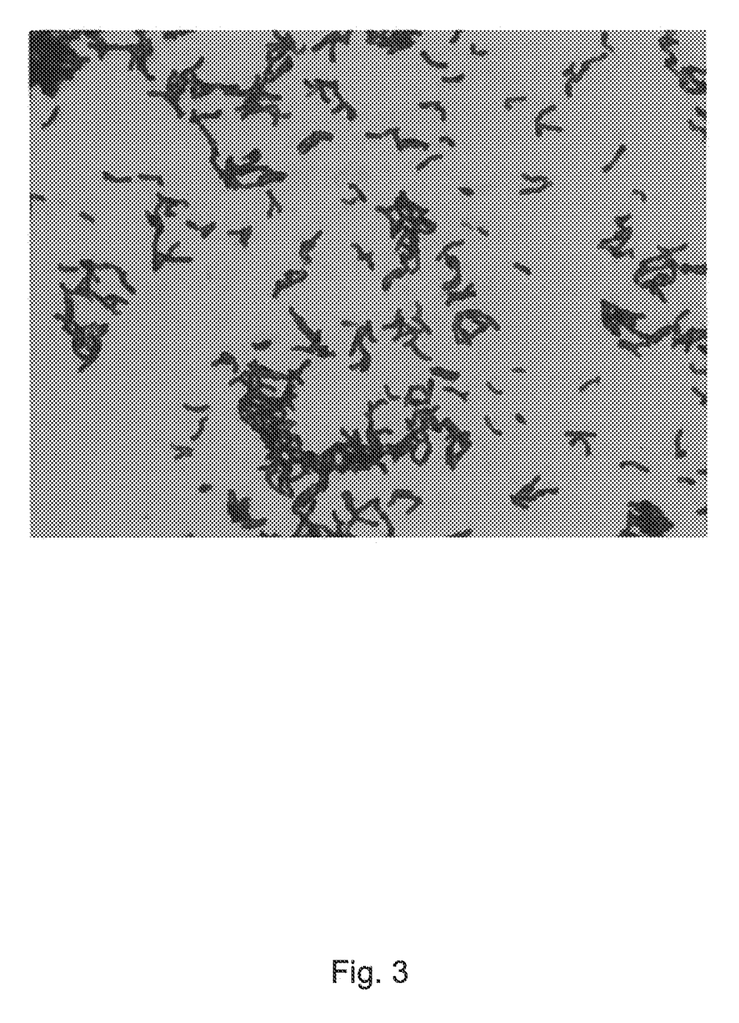
FIG. 3 is a picture of isolated *Bifidobacterium bifidum* PM-A0218 under microscope.

The picture of the isolated bacteria under microscope is shown in FIG. 3. The isolated bacteria are rod-shaped or Y-shaped Gram-positive bacteria. This strain of bacteria was identified as *Bifidobacterium bifidum* and designated as PM-A0218, and was deposited with the Agricultural Research Culture Collection and have been assigned deposit number NRRLB-505241.

Example 2

Effects of the Composition Comprising One Biologically Pure Culture of *Lactobacillus plantarum* subsp. *plantarum* PM-A0087, *Bifidobacterium longum* PM-A0101, *Bifidobacterium bifidum* PM-A0218, or a Combination Thereof in Preventing NEC Preparation of the Cultures of the Strains
*Lactobacillus plantarum* subsp. *plantarum* PM-A0087 was cultured in MRS medium at 37° C. *Bifidobacterium longum* PM-A0101 and *Bifidobacterium bifidum* PM-A0218 were cultured in MRS medium supplemented with 5% Cysteine at 37° C. in anaerobic condition. After a culture for 3 days, the cells of each strain in the bacterial culture tube were dispersed thoroughly and subjected to optical density (OD) measurement to evaluate the number of bacteria. Then, each of the cultures was adjusted to $1.5 \times 10^9$ CFU/ml, and 1 ml of the culture was taken and centrifuged at 3,000 rpm for 10 minutes. The supernatant was removed, and refrigerated at 4° C. for 30 minutes, and then moved for storage at −20° C. Before feeding the animals, the cultures of *Lactobacillus plantarum* subsp. *plantarum* PM-A0087, *Bifidobacterium longum* PM-A0101, and *Bifidobacterium bifidum* PM-A0218 were removed from the −20° C. refrigerator and mixed with 1 mL milk.

Preparation of the NEC Pathogenic Composition
Single colonies of *Klebsiella pneumonia*, *Serratia marcescens*, and *Escherichia coli* were added to 5 mL normal saline, respectively, mixed in 2:2:3, aliquoted into 1.5 mL centrifuge tubes, and stored at 4° C. before use.

Animal Model
Time-dated pregnant Sprague-Dawley rats were anesthetized with $CO_2$ anesthesia (50 seconds) on the 21st day of gestation and delivered via abdominal incision. Newborn rats were collected and placed in a neonatal incubator for humidification and temperature control. Animals were randomly divided into experimental group and control group. At 3 hours of life, animals were fed with 50 µl of the NEC pathogenic composition. At 6 hours of life, animals were fed with 50 µl of milk, or 50 µl of milk comprising any one of the three lactic bacterial strains. Then animals were stressed with asphyxia twice daily by breathing 100% nitrogen gas for 60 seconds and then cold exposure to 4° C. for 10 minutes. At 9 hours of life, animals were fed with 50 µl of the NEC pathogenic composition, and at 12 hours Of life, animals were fed with 50 µl of milk, or 50 µl of milk comprising any one of the three lactic bacterial strains. By the 24 hours of life, animals developed clinical and pathological signs similar to neonatal NEC, e.g. bloody stools, shortness of breath, poor tolerance to feedings, and weight loss.

Upon death of the newborn rats, the small intestine and colon were collected and fixed; histological sections were prepared and subjected to evaluation of the degree of intestinal necrosis.

Results

Figure 4:
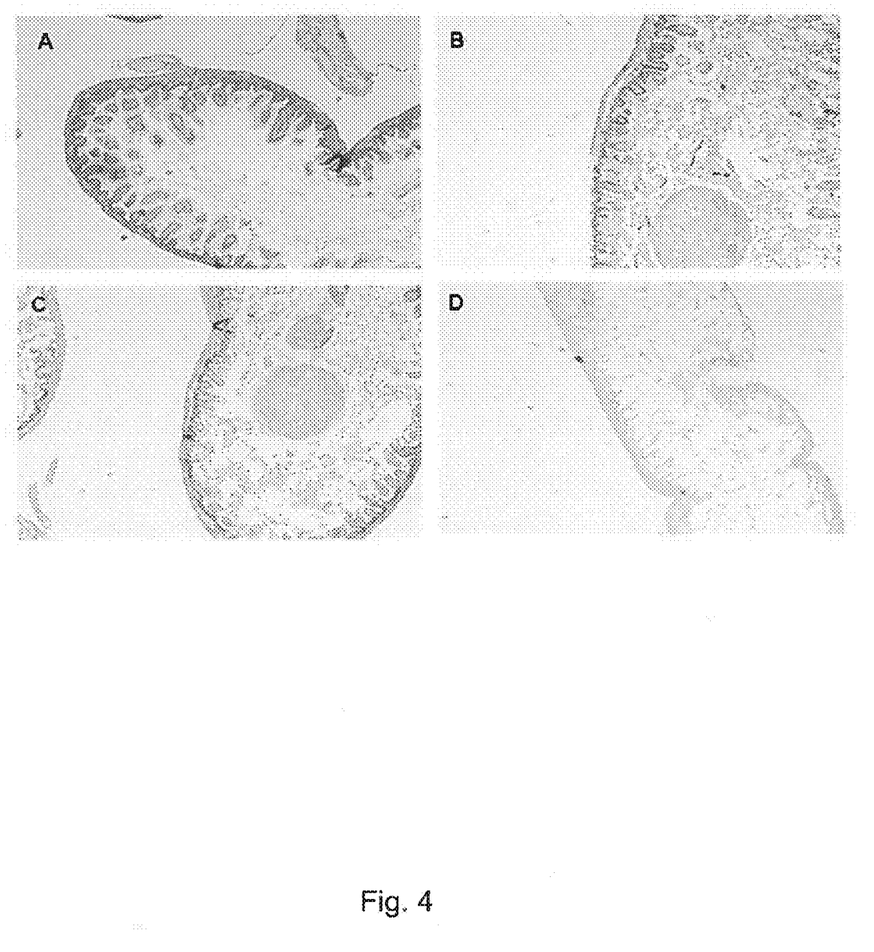
FIG. 4 shows histological sections of the intestines of the animals with different degrees of intestinal necrosis.

As shown in FIG. 4, histological findings were scored by a second blinded observer as follows: 0, no necrosis (FIG. 4A); 1, mild with epithelial sloughing (FIG. 4B); 2, moderate with mid-villous necrosis (FIG. 4C); and 3, severe with total villous necrosis (FIG. 4D). The results are given in Table 1 below.

TABLE 1

Evaluation of the degree of intestinal necrosis.

| | Number of animals (n) | Degree of intestinal necrosis | | | |
|---|---|---|---|---|---|
| | | 0 | 1 | 2 | 3 |
| Control group | 13 | 1 | 3 | 3 | 6 |
| Experiment group 1 (fed with milk comprising *Lactobacillus plantarum* subsp. *plantarum* PM-A0087) | 16 | 10 | 2 | 1 | 3 |
| Experiment group 2 (fed with milk comprising *Bifidobacterium longum* PM-A0101) | 16 | 11 | 0 | 1 | 4 |
| Experiment group 3 (fed with milk comprising *Bifidobacterium bifidum* PM-A0218) | 13 | 7 | 2 | 2 | 2 |
| Experiment group 4 (fed with milk comprising *Bifidobacterium longum* PM-A0101 and *Bifidobacterium bifidum* PM-A0218) | 12 | 9 | 1 | 0 | 2 |
| Experiment group 5 (fed with milk comprising *Lactobacillus plantarum* subsp. *plantarum* PM-A0087, *Bifidobacterium longum* PM-A0101 and *Bifidobacterium bifidum* PM-A0218) | 12 | 7 | 1 | 3 | 1 |

The results were subject to nonparametric Mann-Whitney test using SPSS 12.0 (p-value<0.05 indicates statistical significance, see Table 2 below).

TABLE 2

Statistical analysis of the results (*, $p < 0.05$; **, $p < 0.01$).

| | Number of animals (n) | Mean degree of intestinal necrosis | Significance compared to control group (U-test) |
|---|---|---|---|
| Control group | 13 | 2.0769 | |
| Experiment group 1 (fed with milk comprising *Lactobacillus plantarum* subsp. *plantarum* PM-A0087) | 16 | 0.8125 | $P = 0.009$** |
| Experiment group 2 (fed with milk comprising *Bifidobacterium longum* PM-A0101) | 16 | 0.8750 | $P = 0.02$* |
| Experiment group 3 (fed with milk comprising *Bifidobacterium bifidum* PM-A0218) | 13 | 0.9231 | $P = 0.019$* |
| Experiment group 4 (fed with milk comprising *Bifidobacterium longum* PM-A0101 and *Bifidobacterium bifidum* PM-A0218) | 12 | 0.5833 | $P = 0.005$** |
| Experiment group 5 (fed with milk comprising *Lactobacillus plantarum* subsp. *plantarum* PM-A0087, *Bifidobacterium longum* PM-A0101 and *Bifidobacterium bifidum* PM-A0218) | 10 | 0.4167 | $P = 0.002$** |
| Total | 82 | | |

Figure 5:
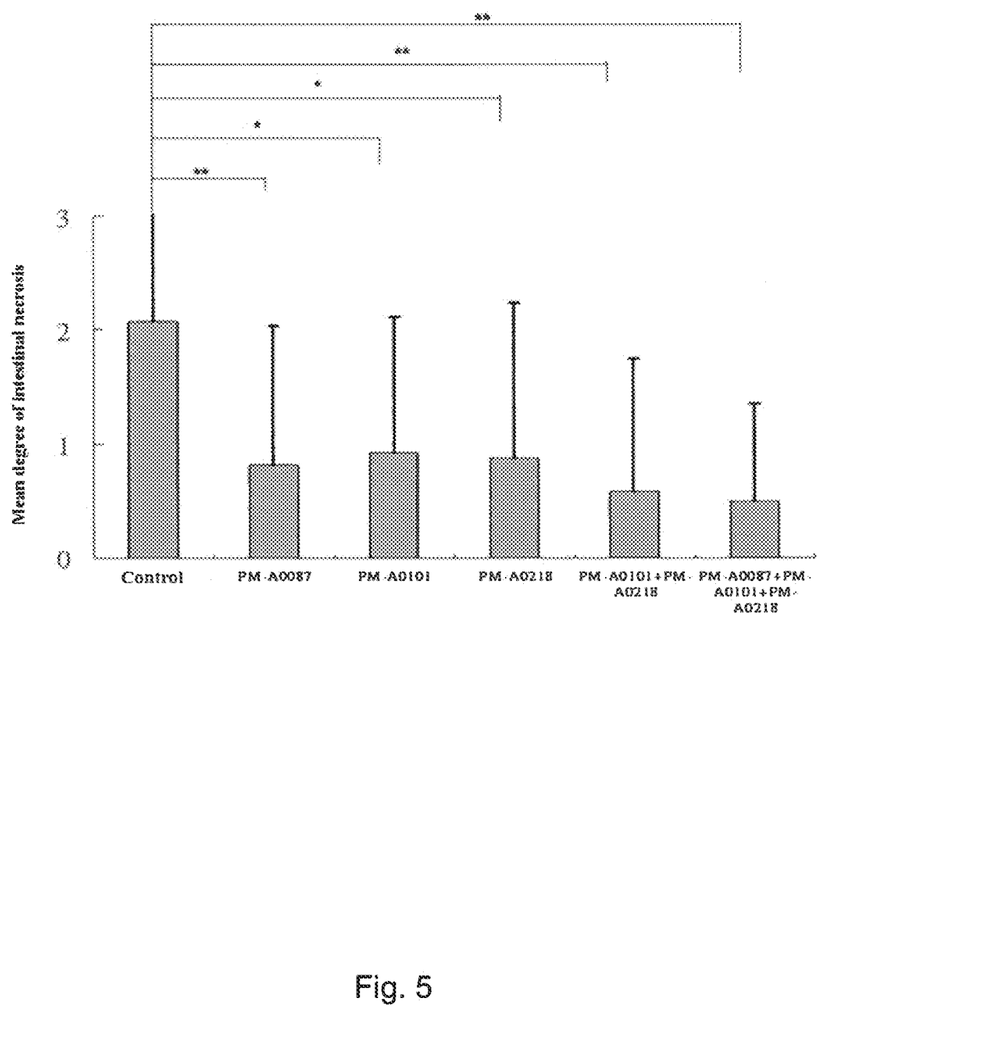
FIG. 5 shows the means of the intestinal necrosis levels in the newborn rats of control group or experimental groups fed with the compositions comprising either of the biologically pure cultures of *Lactobacillus plantarum* subsp. *plantarum* PM-A0087, *Bifidobacterium longum* PM-A0101, and *Bifidobacterium bifidum* PM-A0218, or their combination.

As shown in Table 1, Table 2 and FIG. 5, composition comprising a biologically pure culture of *Lactobacillus plantarum* subsp. *plantarum* PM-A0087, a biologically pure culture of *Bifidobacterium longum* PM-A0101, a biologically pure culture of *Bifidobacterium bifidum* PM-A0218, or a combination thereof is effective in preventing NEC of newborn rats, as compared to the control group.

It was concluded that the composition comprising each of the strains of the invention or their combination is effective in preventing NEC.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

We claim:

1. An isolated biologically pure culture of a lactic acid bacteria strain selected from the group consisting of:
    *Lactobacillus plantarum* subsp. *plantarum* PM-A0087 deposited as NRRL accession number B-50523;
    *Bifidobacterium longum* PM-A0101 deposited as NRRL accession number B-50525; and
    *Bifidobacterium bifidum* PM-A0218 deposited as NRRL accession number B-50524.

2. A composition, comprising an isolated biologically pure culture of *Lactobacillus plantarum* subsp. *plantarum* PM-A0087 deposited as NRRL accession number B-50523, *Bifidobacterium longum* PM-A0101 deposited as NRRL accession number B-50525, *Bifidobacterium bifidum* PM-A0218 deposited as NRRL accession number B-50524, or a combination thereof.

3. The composition according to claim 2, comprising a biologically pure culture of *Lactobacillus plantarum* subsp. *plantarum* PM-A0087 deposited as NRRL accession number B-50523, a biologically pure culture of *Bifidobacterium longum* PM-A0101 deposited as NRRL accession number B-50525, and a biologically pure culture of *Bifidobacterium bifidum* PM-A0218 deposited as NRRL accession number B-50524.

4. The composition according to claim 2, comprising a biologically pure culture of *Lactobacillus plantarum* subsp. *plantarum* PM-A0087 deposited as NRRL accession number B-50523, a biologically pure culture of *Bifidobacterium longum* PM-A0101 deposited as NRRL deposit number B-50525, and a biologically pure culture of *Bifidobacterium bifidum* PM-A0218 deposited as NRRL deposit number B-50524 respectively, wherein the composition comprises an equal number of cells from each biologically pure culture.

5. The composition according to claim 2, wherein each of the biologically pure cultures of the strains contains $0.1–10 \times 10^9$ CFU/ml bacteria.

6. The composition according to claim 5, wherein each of the biological pure cultures of the strains contains about $1 \times 10^9$ CFU/ml bacteria.

7. The composition according to claim 5, wherein each of the biological pure cultures of the strains contains about $1.5 \times 10^9$ CFU/ml bacteria.

8. The composition according to claim 2 for oral administration.

9. The composition according to claim 2, which is a pharmaceutical composition.

10. The composition according to claim 2, which is a dietary composition.

\* \* \* \* \*